United States Patent
Wang et al.

(10) Patent No.: US 12,110,544 B2
(45) Date of Patent: Oct. 8, 2024

(54) METHOD FOR EXTRACTING TOTAL MICROBIAL DNA FROM MILK

(71) Applicant: INSTITUTE OF ANIMAL SCIENCES, CHINESE ACADEMY OF AGRICULTURAL SCIENCES, Beijing (CN)

(72) Inventors: Jiaqi Wang, Beijing (CN); Shengguo Zhao, Beijing (CN); Nan Zheng, Beijing (CN); Xu Zhou, Beijing (CN); Songli Li, Beijing (CN)

(73) Assignee: INSTITUTE OF ANIMAL SCIENCES, CHINESE ACADEMY OF AGRICULTURAL SCIENCES, Beijing (CN)

( * ) Notice: Subject to any disclaimer, the term of this patent is extended or adjusted under 35 U.S.C. 154(b) by 988 days.

(21) Appl. No.: 17/058,964

(22) PCT Filed: Jul. 13, 2018

(86) PCT No.: PCT/CN2018/095679
§ 371 (c)(1),
(2) Date: Nov. 25, 2020

(87) PCT Pub. No.: WO2019/223084
PCT Pub. Date: Nov. 28, 2019

(65) Prior Publication Data
US 2021/0292809 A1   Sep. 23, 2021

(30) Foreign Application Priority Data

May 25, 2018 (CN) .......................... 201810515008.X

(51) Int. Cl.
*C12Q 1/686* (2018.01)
*C12N 15/10* (2006.01)
*C12Q 1/6806* (2018.01)

(52) U.S. Cl.
CPC ......... *C12Q 1/686* (2013.01); *C12N 15/1003* (2013.01); *C12Q 1/6806* (2013.01)

(58) Field of Classification Search
CPC ...... C12Q 1/686; C12Q 1/6806; C12Q 1/689; C12Q 1/06; C12N 15/1003
See application file for complete search history.

(56) References Cited

U.S. PATENT DOCUMENTS

2015/0056624 A1*   2/2015   Cramer .............. C12N 15/1003
                                                        435/6.15

FOREIGN PATENT DOCUMENTS

| CN | 1544941 A | 11/2004 |
| CN | 102174509 A | 9/2011 |
| CN | 103993071 A | 8/2014 |
| CN | 106497913 A | 3/2017 |

OTHER PUBLICATIONS

Cenci-Goga BT et al. Detection of tet(M) Gene from Raw Milk by Rapid DNA Extraction Followed by a Two-Step PCR with Nested Primers. 2004. Journal of Food Protection. vol. 67, No. 12. p. 2833-2838. (Year: 2004).*
Mukhopadhyay T et al. Silicone lubricant enhances recovery of nucleic acids after phenol-chloroform extraction. 1993. Nucleic Acids Research. vol. 21, No. 3. p. 781-782. (Year: 1993).*
Promega. TE Buffer. 2024. p. 1-5. (Year: 2024).*
CN103993071A machine translation generated in Espacenet. p. 1-16. (Year: 2014).*

* cited by examiner

*Primary Examiner* — Paul J Holland
(74) *Attorney, Agent, or Firm* — NKL Law; Allen Xue

(57) ABSTRACT

In a method for extracting microbial DNA from milk, the extracted DNA can be directly used for PCR amplification. The method includes the following steps: treating milk with TE solution, fully disrupting microbial cells by bead milling, immobilizing proteins in the middle layer between the aqueous and organic phases with high-vacuum silicone grease so as to prevent impurities in the middle layer from entering the aqueous phase, etc. The extracted DNA has a high degree of intactness, high concentration and purity.

9 Claims, 1 Drawing Sheet

Specification includes a Sequence Listing.

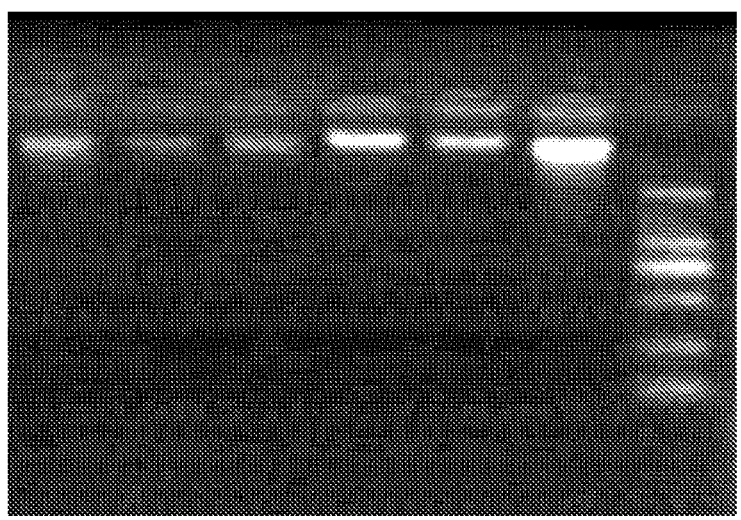

SEQUENCE LISTING

<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: synthesized.

<400> SEQUENCE: 1
agagtttgat cctggctcag                                                  20

<210> SEQ ID NO 2
<211> LENGTH: 19
<212> TYPE: DNA
<213> ORGANISM: Artificial sequence
<220> FEATURE:
<223> OTHER INFORMATION: synthesized.

<400> SEQUENCE: 2
ggttaccttg ttacgactt                                                   19

METHOD FOR EXTRACTING TOTAL MICROBIAL DNA FROM MILK

CROSS-REFERENCE OF RELATED APPLICATIONS

The present application is a U.S. national phase entry of international application no. PCT/CN2018/095679, filed on Jul. 13, 2018, which claims the priority of the earlier Chinese application No. 201810515008.X submitted to China National Intellectual Property Administration on May 25, 2018, which is entitled "Method for extracting total microbial DNA from milk". The entire content of the earlier application is incorporated herein by reference.

Incorporation of Sequence Listing

This application contains a sequence listing submitted in Computer Readable Form (CRF). The CFR file containing the sequence listing entitled "PA150-0087_ST25.txt", which was created on Jun. 7, 2021, and is 768 bytes in size. The information in the sequence listing is incorporated herein by reference in its entirety.

FIELD OF THE INVENTION

The invention belongs to the field of food quality and safety, and specifically relates to a method for extracting total microbial genomic DNA from milk, and identifying microbial species in milk after PCR amplification with the DNA as a template.

BACKGROUND OF THE INVENTION

Milk is the raw material for dairy products. The quality and safety of milk are essential, which directly influence the quality and safety of downstream products. Whether or not milk contains microorganisms, and the types and quantities of microorganisms contained are important indicators for evaluating milk quality. Since most of the microorganisms cannot be identified by culture method, it is impossible to identify all types of microorganisms that may be contained in milk only by culture method. Currently, a large number of uncultured microorganisms have been effectively identified by PCR amplification and identification, but the method requires a relatively high amount and purity of the microbial DNA extracted from milk. Therefore, for this method, the extraction of microbial DNA is the first critical step.

At present, the prior art methods for extracting milk microbial DNA are generally complicated and costly, and can extract only one or several types of microbial DNA from milk. Moreover, due to the problems such as incomplete removal of milk proteins, poor cell disruption efficiency and high levels of residual impurities, the milk microbial DNA obtained has low concentration and purity, and can easily lead to false negative results. Therefore, it is necessary to find a simple, rapid and efficient method for extracting total microbial DNA from milk.

SUMMARY OF THE INVENTION

An object of the invention is to provide a simple, rapid and efficient method for extracting total microbial DNA from milk. The DNA extracted by the method has a high degree of intactness, long sequences, high concentration and purity, which can be directly used for PCR amplification and meet the needs of identifying total microbial species in milk.

According to one aspect of the invention, a method for extracting total microbial DNA from milk is provided, which comprises the following steps:
(1) milk pre-treatment: placing milk samples in centrifuge tubes, centrifuging, discarding the supernatant, removing fat, adding TE solution, repeatedly pipetting up and down with a pipetting gun until the precipitate is completely dissolved, centrifuging, discarding the supernatant, removing residual fat, and retaining the precipitate;
(2) microbial lysis: adding CTAB lysate into the precipitate obtained in step (1), repeatedly pipetting up and down with a pipetting gun until precipitate is completely dissolved, adding glass beads, disrupting cells in a bead mill, adding a proteinase K solution, placing in water bath, centrifuging, and taking the supernatant for use;
(3) DNA purification: adding an equal volume of a mixed solution of phenol: chloroform: isoamyl alcohol to the supernatant obtained in step (2), vortex mixing until a white emulsion is obtained, adding appropriate amount of high-vacuum silicone grease, centrifuging, taking the upper aqueous phase, adding cold isopropanol, mixing the mixture upside and down, letting it stand, centrifuging, discarding the supernatant, adding an ethanol aqueous solution to wash the precipitate, centrifuging, discarding the supernatant, placing the precipitate on a filter paper, and drying at room temperature to obtain the milk total microbial DNA.

According to another aspect of the invention, a method for identifying microbial species in milk is provided, which further comprises the following step on the basis of the above steps: (4) identification of microbial species: dissolving the milk total microbial DNA obtained in step (3) with TE solution, performing PCR amplification, performing recovery and purification with PCR product purification kits, sequencing, and then identifying microbial species in milk.

In step (1), the amount of the milk sample is preferably 1-10 ml, more preferably 7 ml; the milk sample is centrifuged preferably at 12000-15000 g before and after the addition of TE solution, more preferably at 14000 g, and the centrifugation time is preferably 3-10 min, more preferably 5 min; the fat and residual fat are removed preferably by using sterile cotton swabs; the amount of the TE solution added is preferably 1-5 ml, more preferably 3 ml; the TE solution is preferably 1-20 mM Tris-HCl, 0.5-5 mM EDTA or disodium EDTA, pH 7-9; more preferably, the TE solution is 10 mM Tris-HCl, 1 mM EDTA or disodium EDTA, pH 8.

In step (2), the volume of the CTAB lysate is preferably 500-1500 μl, more preferably 1000 μl; the diameter of the glass beads is preferably 0.01-0.1 mm, more preferably 0.05 mm; the cell disruption is performed preferably at 10-30 m/s, more preferably 30 m/s, and the time is preferably 0.5-2 min, more preferably 1 min; the cell disruption is performed preferably 1-3 times, more preferably twice, preferably with a pause of 30 s-5 min, more preferably with a pause of 1 min; the proteinase K solution is preferably an aqueous solution of proteinase K, and the concentration of the proteinase K solution is preferably 10-50 mg/ml, more preferably 20 mg/ml, and the amount of the proteinase K solution added is preferably 10-50 μl, more preferably 20 μl; preferably, firstly, proteinase K is used to hydrolyze the residual proteins in a 52-58° C. water bath for 20-40 min, and then CTAB lysate is used to lyse the cells in a 65-75° C. water bath for 10-30 min; more preferably, the mixture is firstly kept in a 55° C. water bath for 30 min, and then in a 70° C.

water bath for 20 min; the mixture is mixed preferably every 5-10 min in the water bath, more preferably every 5 min; the mixture is centrifugated preferably at 12000-15000 g, more preferably at 14000 g, and the centrifugation time is preferably 1-10 min, more preferably 5 min; preferably, the CTAB lysate contains 1.4 M NaCl, 100 mM Tris-HCl (pH 8.0), 20 mM EDTA or disodium EDTA (pH 8.0) and 2% CTAB.

In step (3), the ratio of each component in the mixed solution of phenol:chloroform:isoamyl alcohol is 25:24:1; the solution is vortex mixed for 2-10 s, preferably 3-5 s; the amount of the high-vacuum silicone grease added is preferably 0.1-0.3 g, more preferably 0.2 g; the centrifugation performed before and after the addition of isopropanol, and after being washed with the ethanol aqueous solution, is preferably carried out at 12000-15000 g, more preferably at 14000 g; the centrifugation time before the addition of isopropanol is preferably 1-10 min, more preferably 5 min, the centrifugation time after the addition of isopropanol is preferably 10-20 min, more preferably 15 min; the centrifugation is performed preferably at 4° C.; the centrifugation time after being washed with the ethanol aqueous solution is preferably 5-15 min, more preferably 10 min; the amount of isopropanol added is preferably 0.6-1 times the volume of the upper aqueous phase u, more preferably 0.8 times; the temperature of isopropanol is preferably 0-20° C., more preferably 4° C.; the standing time is preferably 15 min-1 h, more preferably 30 min, and the standing is carried out preferably at 4° C.; the concentration of the ethanol aqueous solution is preferably 60-80%, more preferably 70%; the amount of the aqueous solution of ethanol added is preferably 500-1000 μl, more preferably 800 μl; the drying time is preferably 15 min-1 h, more preferably 20 min.

In step (4), the TE solution is 10 mM Tris-HCl, 1 mM EDTA or disodium EDTA, pH 8; the amount of the TE solution added is preferably 50-150 μl, more preferably 100 μl. Preferably, the upstream primer for PCR amplification is 27F: 5'-AGAGTTTGATCCTGGCTCAG-3', SEQ ID NO: 1 and the downstream primer is 1492R: 5'-GGTTACCTTGT-TACGACTT-3', SEQ ID NO: 2.

It should be understood by those skilled in the art that in the invention, the total microbial DNA extracted from milk can be amplified by using PCR amplification systems and reaction conditions commonly used in the art; the recovery and purification of the amplified DNA can be performed with PCR product purification kits commonly used in the art, for example, Axygen gel recovery and purification kits, etc.; the sequencing of DNA can be performed by conventional methods in the art, such as PacBio third-generation sequencers, second-generation sequencers, etc.; after sequencing DNA, microbial species can be identified by conventional methods in the art, such as the online RDP Classifier.

The method of the invention is suitable for extracting the total microbial genomic DNA in milk, convenient for sampling, practical, easy in operation, and low in cost. The total microbial DNA in milk can be extracted quickly and efficiently with high extraction efficiency by the method. The extracted DNA has a high degree of intactness, long sequences, high concentration and high purity. Compared with the prior art, the technological innovation is reflected in the following aspects:

1. Owning to the high extraction efficiency of the method of the invention, the amount of the milk used can be controlled within 10 ml, such as 7 ml; the concentration and purity of the extracted DNA are high; and the sampling is convenient and rapid.

2. TE solution is used for treating milk to disrupt the casein micelles, dissolve the casein precipitates, and reduce protein impurities. The residual proteins are further degraded by adding proteinase K to reduce DNA contamination.

3. Bead milling is used to completely disrupt microbial cells, and release DNA, which overcomes the problem of poor microbial cell-disrupting efficiency of the prior art methods.

4. High-vacuum silicone grease is used to immobilize proteins in the middle layer between the aqueous and organic phases so as to prevent impurities in the middle layer from entering the aqueous phase.

5. The extracted DNA has high concentration and high purity, and can be directly used for PCR amplification and sequencing analysis.

6. The total microbial DNA extracted from milk can used to identify known and unknown microorganisms contained in milk.

BRIEF DESCRIPTION OF THE DRAWING

FIG. 1. Agarose gel (1.5%) electrophoresis result of the DNA extracted by the method of the invention.

EXAMPLES

Hereinafter, the technical solutions of the invention will be further illustrated in detail with reference to the specific examples. It should be understood that the examples are intended to give an illustration of the invention, rather than set any limitation on the protection scope of the invention. In addition, it should be understood that after reading the content of the invention, a person skilled in the art can make various changes and modifications to the invention, and these equivalents are also deemed to fall within the scope of the invention.

1. Experimental Instruments
    Bead mill (MM 400) (Retsch)
    PCR Instrument (T100) (Bio-Rad)
    Horizontal plate electrophoresis chamber (Bio-Rad)
    Gel Imaging System (Bio-Rad VersaDoc)
    Ultrapure Water Purification System (Milli-Q) (Millipore)
    Vortex Mixer (Vortex-Genie2) (Scientific Industries)
2. Main Reagents
    The chemical reagents used in the following examples are all conventional reagents and commercially available.
3. Preparation of the Solutions
    1) High-vacuum silicone grease: Dow Corning, directly used.
    2) 1 mol/L Tris-HCl (pH 8.0): 42 mL concentrated HCl was added to 121.1 g of Tris base to make a volume of 1 L; the mixture was adjusted to a pH of 8.0 with concentrated HCl, and then was autoclaved at 121° C. for 15 min.
    3) CTAB lysate (pH 8.0): 1.4 mol/L NaCl, 100 mmol/L Tris-HCl (pH 8.0), 20 mmol/L EDTA (pH 8.0), and 2% CTAB were mixed well and then autoclaved at 121° C. for 15 min.
    4) 0.5 mol/L disodium EDTA (pH 8.0): water was added to 186.1 g disodium EDTA and 20 g NaOH under vigorous stirring to make a volume of 1 L; the mixture was adjusted to a pH of 8.0 with NaOH, and then was autoclaved at 121° C. for 15 min.
    5) TE solution (pH 8.0): 10 mL 1M Tris-HCl (pH 8.0) and 2 mL 0.5M EDTA (pH 8.0) were mixture and then ultrapure water was added to make a volume of 1 L; and the obtained mixture was autoclaved at 121° C. for 15 min.

6) 20 mg/mL proteinase K: 20 mg of proteinase K was dissolved in ultrapure water and mixed well. The obtained solution was stored at −20° C.

7) 50×TAE buffer: 242.0 g of Tris base, 57.1 ml of glacial acetic acid, 100 mL of 0.5 M disodium EDTA (pH 8.0) were mixed under heating until the solid was dissolved; water was added to make a volume of 1 L; and then the solution was autoclaved at 121° C. for 15 min.

8) 1×TAE buffer: 2450 mL of ultrapure water was added to 50 mL of 50×TAE buffer and mixed well.

9) 1.5% agarose gel: 1.5 g of agarose was added to 100 mL of 1×TAE electrophoresis buffer under heating until the agarose was dissolved; the solution was cooled down to a temperature of 50 to 60° C., and then 5 mg/mL nucleic acid dye was added (final concentration of 0.5 μg/mL) and mixed well.

Example 1: Extraction of Total Microbial DNA from Milk

1. Milk Pre-Treatment:

The milk sample was thawed at 4° C. 7 ml of the milk sample was placed in a 10 ml centrifugal tube, and centrifuged at 14000 g for 5 min. The supernatant was discarded, and the fat was removed by using sterilized cotton swabs. 3 ml of TE solution was added. The solution was repeatedly pipetted up and down with a pipetting gun to destroy the casein micelles until the precipitate was completely dissolved. The mixture was centrifuged at 14000 g for 5 min. The supernatant was discarded, and the residual fat was removed. The precipitate was retained.

2. Microbial Lysis:

1000 μL of the CTAB lysate was added to the precipitate obtained in step 1. The mixture was repeatedly pipetted up and down with a pipetting gun until the precipitate was completely dissolved. The mixture was transferred to a 2 ml sterile centrifuge tube. Glass beads were added to perform cell disruption (30 m/s, 1 min) in a bead mill. The cell disruption was repeated once more after a pause of 1 min. 20 μL of the proteinase K solution was added. The mixture was placed in a 55° C. water bath for 30 min, and mixed every 5-10 min. The proteins were removed and DNA was released. The mixture was placed in a 70° C. water bath for 20 min, mixed every 5 min, and centrifuged at 14000×g for 5 min. 800 μL of the supernatant was pipetted for use.

3. DNA Purification:

To the supernatant obtained in step 2, an equal volume of the solution of phenol: chloroform: isoamyl alcohol (25:24:1) was added. The mixture was vortex mixed (3-5 s) until a white emulsion was obtained. Around 0.2 g of high-vacuum silicone grease was added to separate the aqueous and organic phases. The mixture was centrifuged at 14000×g at room temperature for 5 min. 700 μL of the upper aqueous phase was pipetted to a 1.5 mL sterile centrifuge tube, and 0.8 times volume of cold isopropanol was added. The mixture was mixed upside and down, allowed to stand at 4° C. for 30 min, and centrifuged at 14000×g at room temperature for 5 min. The supernatant was poured out carefully. The precipitate was washed with 800 μL of 70% ethanol solution, and centrifuged at 14000×g for 10 min. The supernatant was poured out carefully. The centrifuge tube was put upside down on a clean filter paper. The precipitate was dried at room temperature for 20 min to obtain the milk total microbial DNA.

4. DNA Quality Inspection:

The DNA was dissolved in 100 μL of TE solution. The DNA concentration was measured at 260 nm in Nanodrop 1000. The DNA purity was evaluated by electrophoresis on a 1.5% agarose gel. Part of the results were shown in FIG. 1. The DNA bands were clear and intact, with no obvious tailing and dispersion.

The DNA concentration measured in a Nanodrop One instrument was around 53.2 ng/μl. The DNA purity was measured in the Nanodrop One instrument, and the OD260/OD280 was about 1.86.

Note: OD260/OD280 was usually used to evaluate DNA purity. The appropriate OD260/OD280 ratio is within the range of 1.8 to 2.0, below 1.8 indicating protein contamination, and above 2.0 indicating RNA contamination.

Example 2: Identification of Microbial Species in Milk

1. Primer Design and Synthesis

Upstream primer: 27F: 5'-AGAGTTTGATCCTGGCTCAG-3', SEQ ID NO: 1;

Downstream primer: 1492R: 5'-GGTTACCTTGTTACGACTT-3', SEQ ID NO: 2.

2. PCR Reaction

The DNA dissolved in 100 μL of TE solution in step 4 of Example 1 was used as the DNA template for PCR amplification.

The PCR reaction system had a volume of 50 μL and contained the following solutions or reagents:

3 μL DNA template, 2 μL upstream primer (200 nM), 2 μL downstream primer (200 nM), 5 L dNTPs (10 μM), 10 μL 5×PCR buffer, 0.4 μL high-fidelity Taq DNA polymerase (Takara), and the balance of PCR-grade sterile water.

The PCR reaction conditions were set as follows:

Pre-denaturation at 95° C. for 3 min; denaturation at 95° C. for 30 s; renaturation at 55° C. for 30 s, extension at 72° C. for 1 min, 30 cycles; storage at 4° C. after extension at 72° C. for 10 min.

The PCR product was identified by electrophoresis:

1.5% agarose gel was prepared, and a voltage of 90 V was applied. The PCR product was subjected to electrophoresis for 50 min, stained with nucleic acid dye for 30 min, and then observed for bands with gel image analyzer.

3. PCR Product Sequencing and Microbial Species Analysis

The amplified and sequenced product of the primer was recovered and purified with Axygen gel recovery and purification kits. PacBio third-generation sequencer was used to sequence, and then the obtained sequences were identified to microbial species in milk by using the online RDP Classifier, as shown in Table 1.

| Number | Phylum | Class | Order | Family | Genus | Species |
|---|---|---|---|---|---|---|
| 1 | Actinobaceteria | Actinobaceteria | Actinomycetales | Micrococcaceae | *Kocuria* | Unknown |
| 2 | Bacteroidetes | Bacteroidia | Bacteroidales | Bacteroidaceae | 5-7N15 | Unknown |
| 3 | Bacteroidetes | Bacteroidia | Bacteroidales | Porphyromonadaceae | *Porphyromonas* | Unknown |
| 4 | Bacteroidetes | Bacteroidia | Bacteroidales | Unknown | Unknown | Unknown |

-continued

| Number | Phylum | Class | Order | Family | Genus | Species |
|---|---|---|---|---|---|---|
| 5 | Firmicutes | Bacilli | Bacillales | Bacillaceae | *Bacillus* | *cereus* |
| 6 | Firmicutes | Bacilli | Bacillales | Staphylococcaceae | *Macrococcus* | *caseolyticus* |
| 7 | Firmicutes | Bacilli | Lactobacillales | Aerococcaceae | *Aerococcus* | Unknown |
| 8 | Firmicutes | Bacilli | Lactobacillales | Aerococcaceae | Unknown | Unknown |
| 9 | Firmicutes | Bacilli | Lactobacillales | Enterococcaceae | *Enterococcus* | Unknown |
| 10 | Firmicutes | Bacilli | Lactobacillales | Lactobacillaceae | *Lactobacillus* | Unknown |
| 11 | Firmicutes | Bacilli | Lactobacillales | Streptococcaceae | *Streptococcus* | *dysgalactiae* |
| 12 | Firmicutes | Bacilli | Lactobacillales | Streptococcaceae | *Streptococcus* | Unknown |
| 13 | Firmicutes | Clostridia | Clostridiales | Clostridiaceae | *Clostridium* | *perfringens* |
| 14 | Firmicutes | Clostridia | Clostridiales | Lachnospiraceae | *Coprococcus* | Unknown |
| 15 | Firmicutes | Clostridia | Clostridiales | Lachnospiraceae | *Dorea* | Unknown |
| 16 | Firmicutes | Clostridia | Clostridiales | Lachnospiraceae | Unknown | Unknown |
| 17 | Firmicutes | Clostridia | Clostridiales | Peptostreptococcaceae | Unknown | Unknown |
| 18 | Firmicutes | Clostridia | Clostridiales | Rumincoccaceae | Unknown | Unknown |
| 19 | Firmicutes | Clostridia | Clostridiales | Unknown | Unknown | Unknown |
| 20 | Fusobacteria | Fusobacteria | Fusobacteriales | Fusobacteriaceae | *Fusobacterium* | Unknown |
| 21 | Proteobacteria | Alphaproteobacteria | Rickettsiales | Rickettsiaceae | Unknown | Unknown |
| 22 | Proteobacteria | Betaproteobacteria | Burkholderiales | Comamonadaceae | *Curvibacter* | Unknown |
| 23 | Proteobacteria | Betaproteobacteria | Burkholderiales | Comamonadaceae | Unknown | Unknown |
| 24 | Proteobacteria | Betaproteobacteria | Burkholderiales | Oxalobacteraceae | Unknown | Unknown |
| 25 | Proteobacteria | Gammaproteobacteria | Enterobacteriales | Enterobacteriaceae | Unknown | Unknown |
| 26 | Proteobacteria | Gammaproteobacteria | Pseudomonadales | Moraxellaceae | *Acinetobacter* | *johnsonii* |
| 27 | Proteobacteria | Gammaproteobacteria | Pseudomonadales | Moraxellaceae | *Enhydrobacter* | Unknown |
| 28 | Proteobacteria | Gammaproteobacteria | Pseudomonadales | Moraxellaceae | *Psychrobacter* | *sanguinis* |
| 29 | Proteobacteria | Gammaproteobacteria | Pseudomonadales | Moraxellaceae | *Psychrobacter* | Unknown |
| 30 | Proteobacteria | Gammaproteobacteria | Pseudomonadales | Pseudomonadaceae | *Pseudomonas* | *vickerii* |
| 31 | Proteobacteria | Gammaproteobacteria | Pseudomonadales | Pseudomonadaceae | *Pseudomonas* | Unknown |

Example 3

1. Two samples of the same milk were taken, each of 7 ml. The experimental group was extracted for DNA by the same method as used in Example 1. The only difference between the control group and the experimental group was that TE solution was not added during milk pre-treatment of step 1 in the control group.

The DNA extracted from the experimental and control groups were dissolved in 100 μL of TE solution, respectively, and the concentrations and purities of the DNA were determined by the same method as used in Example 1. The concentration of the DNA extracted in the experimental group with TE solution and that of the DNA of the control group without TE solution were 42.5 ng/μl and 21.5 ng/μl, respectively, and the OD260/OD280 ratios were 1.85 and 1.64, respectively.

2. Two samples of the same milk were taken, each of 7 ml. The experimental group was extracted for DNA by the same method as used in Example 1. The only difference between the control group and the experimental group was that proteinase K was not added during microbial lysis of step 2 in the control group.

The DNA extracted from the experimental and control groups were dissolved in 100 μL of the TE solution, respectively, and the concentrations and purities of the DNA were determined by the same method as used in Example 1. The concentration of the DNA extracted in the experimental group with proteinase K and that of the DNA in the control group without proteinase K were 46.3 ng/μl and 26.5 ng/μl, respectively, and the OD260/OD280 ratios were 1.87 and 1.59, respectively.

3. Two samples of the same milk were taken, each of 7 ml. The experimental group was extracted for DNA by the same method as used in Example 1. The only difference between the control group and the experimental group was that the bead mill was not used during microbial lysis of step 2 in the control group.

The DNA extracted from the experimental and control groups were dissolved in 100 μL of the TE solution, respectively, and the concentrations and purities of the DNA were determined by the same method as used in Example 1. The concentration of the DNA extracted in the experimental group by using a bead mill and that of the DNA in the control group without using a bead mill were 50.3 ng/μl and 18.1 ng/μl, respectively, and the OD260/OD280 ratios were 1.90 and 1.78, respectively.

4. Two samples of the same milk were taken, each of 7 ml. The experimental group was extracted for DNA by the same method as used in Example 1. The only difference between the control group and the experimental group was that high-vacuum silicone grease was not added during step 3 in the control group.

The DNA extracted from the experimental and control groups were dissolved in 100 μL of the TE solution, respectively, and the concentrations and purities of the DNA were determined by the same method as used in Example 1. The concentration of the DNA extracted in the experimental group with high-vacuum silicone grease and that of the DNA in the control group without high-vacuum silicone grease were 45.2 ng/μl and 40.1 ng/μl, respectively, and the OD260/OD280 ratios were 1.86 and 1.64, respectively.

5. Four samples of the same milk were taken, each of 1 ml, 5 ml, 7 ml, and 10 ml, respectively. DNA was extracted by the same method as used in Example 1, and 100 μL of TE solution was added to the obtained DNA. The concentrations and purities of the DNA were determined by the same method as used in Example 1. The concentrations of the DNA extracted in the groups of 1 ml, 5 ml, 7 ml, and 10 ml, were 10.2 ng/μl, 21.1 ng/μl, 46.1 ng/μl, 49.1 ng/μl, respectively, and the OD260/OD280 ratios were 1.84, 1.94, 1.91, 1.83, respectively.

6. Two samples of the same milk were taken, each of 7 ml. The experimental group was extracted for DNA by the same method as used in Example 1, and the control group used Milk Bacterial DNA Isolation Kit (Norgen, product #21550).

The DNA extracted from the experimental and control groups were dissolved in 100 μL of the TE solution, respectively, and the concentrations and purities of the DNA were determined by the same method as used in Example 1. The concentrations of the DNA extracted in the experimental and the control groups were 50.3 ng/μl and 18.0 ng/μl, respectively, and the OD260/OD280 ratios were 1.86 and 1.88, respectively.

The invention claimed is:

1. A method for identifying microbial species in milk, comprising the following steps:
   (1) milk pre-treatment: placing milk samples in centrifuge tubes, centrifuging, discarding the supernatant, removing fat, adding TE solution, repeatedly pipetting up and down with a pipetting gun until the precipitate is completely dissolved, centrifuging, discarding the supernatant, removing residual fat, and retaining the precipitate;
   (2) microbial lysis: adding CTAB lysate into said precipitate obtained in step (1), repeatedly pipetting up and down with a pipetting gun until said precipitate is completely dissolved, adding glass beads, disrupting cells in a bead mill, adding a proteinase K solution, placing in water bath, centrifuging, and taking the supernatant for use;
   (3) DNA purification: adding an equal volume of a mixed solution of phenol: chloroform: isoamyl alcohol to said supernatant obtained in step (2), vortex mixing until a white emulsion is obtained, adding appropriate amount of high-vacuum silicone grease, centrifuging, taking the upper aqueous phase, adding cold isopropanol, mixing the mixture upside and down, letting it stand, centrifuging, discarding the supernatant, adding an ethanol aqueous solution to wash the precipitate, centrifuging, discarding the supernatant, placing the precipitate on a filter paper, and drying at room temperature to obtain the milk total microbial DNA; and
   (4) identification of microbial species: dissolving said milk total microbial DNA obtained in step (3) in TE solution, performing PCR amplification, performing recovery and purification with PCR product purification kits, sequencing, and then identifying microbial species in milk;
   the upstream primer for PCR amplification consists of the nucleotide sequence as shown in SEQ ID NO: 1 and the downstream primer consists of the nucleotide sequence as shown in SEQ ID NO: 2; and
   the amount of the milk sample is 7 ml.

2. The method according to claim 1, wherein, in step (1),
   the milk sample is centrifuged at 12000-15000 g before and after the addition of TE solution, and the centrifugation time is preferably 3-10 min;
   the fat and residual fat are removed by using sterile cotton swabs;
   the amount of the TE solution added is 1-5 ml;
   the TE solution is 1-20 mM Tris-HCl, 0.5-5 mM EDTA or disodium EDTA, pH 7-9.

3. The method according to claim 1, wherein, in step (2),
   the volume of the CTAB lysate is 500-1500 μl;
   the diameter of glass beads is 0.01-0.1 mm;
   the cell disruption is performed at 10-30 m/s, and the time is 0.5-2 min;
   the cell disruption is performed 1-3 times, a pause of 30 s-5 min;
   the proteinase K solution is an aqueous solution of proteinase K;
   the concentration of the proteinase K solution is 10-50 mg/ml;
   the amount of the proteinase K solution added is 10-50 μl;
   the mixture is firstly kept in a 52-58° C. water bath for 20-40 min, and then in a 65-75° C. water bath for 10-30 min;
   the mixture is mixed every 5-10 min in the water bath;
   the mixture is centrifugated at 12000-15000 g, and the centrifugation time is 1-10 min;
   the CTAB lysate contains 1.4 M NaCl, 100 mM Tris-HCl (pH 8.0), 20 mM EDTA or disodium EDTA (pH 8.0) and 2% CTAB.

4. The method according to claim 1, wherein, in step (3), the ratio of each component in the mixed solution of phenol:chloroform:isoamyl alcohol is 25:24:1;

the solution is vortex mixed for 2-10 s;
the amount of the high-vacuum silicone grease added is 0.1-0.3 g;
the centrifugation performed before and after the addition of isopropanol, and after being washed with the ethanol aqueous solution, is carried out at 12000-15000 g; the centrifugation time before the addition of isopropanol is 1-10 min, the centrifugation time after the addition of isopropanol is 10-20 min; the centrifugation is performed preferably at 4° C.; the centrifugation time after being washed with the ethanol aqueous solution is 5-15 min;
the amount of isopropanol added is 0.6-1 times the volume of the upper aqueous phase taken;
the temperature of isopropanol is 0-20° C.;
the standing time is 15 min-1 h, and the standing is carried out at 4° C.;
the concentration of the ethanol aqueous solution is 60-80%; the amount of the ethanol aqueous solution added is 500-1000 µl; and the drying time is 15 min-1 h.

5. The method according to claim 1, wherein, in step (4), the TE solution is 10 mM Tris-HCl, 1 mM EDTA or disodium EDTA, pH 8;
the amount of the TE solution added is 50-150 µl.

6. The method according to claim 5, wherein, in step (4), the amount of the TE solution added is 100 µl.

7. The method according to claim 2, wherein, the milk sample is centrifuged at 14000 g before and after the addition of TE solution, and the centrifugation time is 5 min;
the amount of the TE solution added is 3 ml; and the TE solution is 10 mM Tris-HCl, 1 mM EDTA or disodium EDTA, pH 8.

8. The method according to claim 4, wherein, in step (2), the volume of the CTAB lysate is 1000 µl;
the diameter of glass beads is 0.05 mm;
the cell disruption is performed at 30 m/s, and the time is 1 min;
the cell disruption is performed twice, with a pause of 1 min;
the concentration of the proteinase K solution is 20 mg/ml;
the amount of the proteinase K solution added is 20 µl;
the mixture is firstly kept in a 55° C. water bath for 30 min, and then in a 70° C. water bath for 20 min;
the mixture is mixed every 5 min in the water bath;
the mixture is centrifugated at 14000 g, and the centrifugation time is 5 min.

9. The method according to claim 1, wherein, in step (3), the solution is vortex mixed for 3-5 s;
the amount of the high-vacuum silicone grease added is 0.2 g;
the centrifugation performed before and after the addition of isopropanol, and after being washed with the ethanol aqueous solution, is carried out at 14000 g; the centrifugation time before the addition of isopropanol is 5 min, the centrifugation time after the addition of isopropanol is 15 min; the centrifugation time after being washed with the ethanol aqueous solution is 10 min;
the amount of isopropanol added is 0.8 times the volume of the upper aqueous phase taken;
the temperature of isopropanol is 4° C.;
the standing time is 30 min;
the concentration of the ethanol aqueous solution is 70%; the amount of the ethanol aqueous solution added is 800 µl; and the drying time is 20 min.

* * * * *